United States Patent [19]

Stiehl et al.

[11] Patent Number: 5,350,367

[45] Date of Patent: Sep. 27, 1994

[54] SNAP TOGETHER HYPODERMIC SYRINGE HOLDER

[75] Inventors: Mark A. Stiehl; Eugene Sisto, both of Rochester; William A. Bergstresser, Prattsburg; Ronald R. Vacek, Rochester, all of N.Y.

[73] Assignee: Sterling Winthrop Inc., New York, N.Y.

[21] Appl. No.: 609,963

[22] Filed: Nov. 6, 1990

[51] Int. Cl.$^5$ .............................................. A61M 5/00
[52] U.S. Cl. .................................. 604/232; 604/228; 604/234
[58] Field of Search ............... 604/182, 187, 188, 221, 604/223, 228, 229, 232, 234, 241, 240, 242

[56] References Cited

U.S. PATENT DOCUMENTS

| | | | |
|---|---|---|---|
| 3,811,441 | 5/1974 | Sarnoff | 604/234 |
| 4,490,142 | 12/1984 | Silvern | 604/241 |
| 4,540,405 | 9/1985 | Miller et al. | 604/241 |
| 4,585,445 | 4/1986 | Hadtke | 604/234 |
| 4,767,413 | 8/1988 | Haber et al. | 604/232 |
| 4,931,043 | 6/1990 | Ray et al. | 604/228 |
| 4,952,208 | 8/1990 | Lix | 604/221 |
| 4,966,601 | 10/1990 | Draenert | 604/232 |
| 4,968,305 | 11/1990 | Takahashi et al. | 604/232 |
| 5,002,537 | 3/1991 | Hoffman et al. | 604/232 |

FOREIGN PATENT DOCUMENTS

| | | | |
|---|---|---|---|
| 0493373 | 6/1953 | Canada | 604/240 |
| 8904680 | 6/1989 | United Kingdom | 604/232 |

Primary Examiner—John D. Yasko
Assistant Examiner—Chalin Smith
Attorney, Agent, or Firm—William J. Davis

[57] ABSTRACT

A readily assembleable, snap together hypodermic syringe holder for use in combination with disposable medicament-containing ampoules is adapted to immobilize an ampoule within the syringe holder and provide manual aspirating capability.

7 Claims, 3 Drawing Sheets

SNAP TOGETHER HYPODERMIC SYRINGE HOLDER

FIELD OF THE INVENTION

This invention relates to the field of hypodermic syringe holders for use in combination with disposable medicament-containing ampoules.

BACKGROUND OF THE INVENTION

It is desirable, in medical practice, to provide hypodermic syringes with an aspirating capability so as to enable the medical practitioner, after insertion of the hypodermic needle into the injection site, to determine whether the needle has entered a major blood vessel and, depending upon whether blood is drawn back into the syringe during aspiration, and depending also upon the desired route of administration, to either proceed with the injection or to withdraw the needle and relocate it before injection as appropriate to the circumstances.

In general, aspiration in hypodermic syringes can be achieved by adapting the syringe holder for either manual or self-aspiration, depending upon whether aspiration is achieved by generation of a slight negative pressure in the syringe holder by the slight manual withdrawal of the ampoule piston or whether the slight negative pressure is generated by some mechanical action effected by the particular syringe design.

Self-aspirating syringes are often complex in structure and are therefore usually expensive to manufacture. Manually operable aspirating syringes have the potential for relative simplicity of construction, because those used with disposable medicament-containing ampoules require only a means to securely hold the ampoule in the syringe holder barrel to prevent axial displacement thereof in the holder and a means to affix the end of the plunger rod of the holder to a slidable piston closing the inner end of the ampoule. With such positive engagement between the plunger and the piston, slight withdrawal of the interconnected plunger/piston generates the essential negative pressure in the ampoule required for aspiration.

U.S. Pat. No. 4,585,445 issued Apr. 29,1986 to F. B. Hadtke describes hypodermic syringe holders, which have achieved widespread commercial acceptance, for use in combination with disposable ampoules. The holders immobilize a cartridge ampoule within the holder during use and provide manual aspirating capability. As indicated by FIG. 2 therein, the holder comprises five working parts, i.e., a body portion, a clamping element, a plunger element, a piston engaging means and a boss element. The boss serves to hold all the elements of the syringe holder together and is affixed to the body portion of the holder mechanically, by gluing, or by thermal, solvent or sonic welding. A significant problem with the holder described in U.S. Pat. No. 4,585,445 is that the boss element tends to pop off the holder during actuation, rendering the holder useless. Yet another problem with such holder is that during the welding process, the boss element can get inadvertently welded to the clamping element. Moreover, it is apparent that it would be desirable to provide a syringe holder which accomplishes the objectives described in U.S. Pat. No. 4,585,445 with fewer working parts and which is less expensive to manufacture.

SUMMARY OF THE INVENTION

We have discovered a snap together syringe holder of a simplified and improved construction which solves the problems noted above resulting from the boss element.

More specifically, in accordance with this invention, there is provided a hypodermic syringe holder adapted to receive a disposable ampoule comprising:

a semi-cylindrical body portion having a generally cylindrical head portion, the head portion having on its inside surface a projecting lug;

an axially movable clamping element rotatable about its longitudinal axis within the cylindrical head of the body portion and engageable with the rim of an associated ampoule to securely immobilize the ampoule within the body portion of the syringe holder, the clamping element comprising a barrel portion, a handle portion, a helical groove on the outer surface of the barrel portion, a bore therethrough, and ramp means connecting the helical groove with an end surface of the clamping element, the barrel portion being sized to rotate and translate within the cylindrical head;

a plunger element including a rod portion having on its lower end a piston engaging means, the rod portion and piston engaging means being axially and slidably receivable within the bore of the clamping element;

so that the helical groove is slidably accessible to the lug through the ramp means and engageable with the lug, whereby the lug secures the clamping element to the body portion such that all of the elements of the syringe holder are in cooperative engagement with one another.

It is an advantageous feature of this invention that there is provided a syringe holder of simple construction, i.e., containing just three working parts, which can be easily and economically manufactured in large quantities, e.g., by precision injection molding techniques.

It is another advantageous feature of this invention that there is provided a syringe holder which can be readily assembled, i.e., by snapping together the body portion, clamping element and plunger element.

Yet another advantageous feature of this invention is that there is provided a syringe holder readily adapted to immobilize a cartridge ampoule within the holder during use having manual aspirating capability.

Other advantageous features will become readily apparent upon reference to the following description of the preferred embodiments when read in light of the accompanying drawings.

DETAILED DESCRIPTION OF THE PREFERRED EMBODIMENTS

While this invention is described particularly with respect to a hypodermic syringe holder, it also finds utility in other holders adapted to dispense a fluid from a disposable cartridge.

As used herein, the terms "lower" and "downward" are intended to make reference to the needle end of the syringe holder and associated parts. Conversely, the terms "upper" and "upward" are intended to make reference to the head end of the holder.

Figure 1:
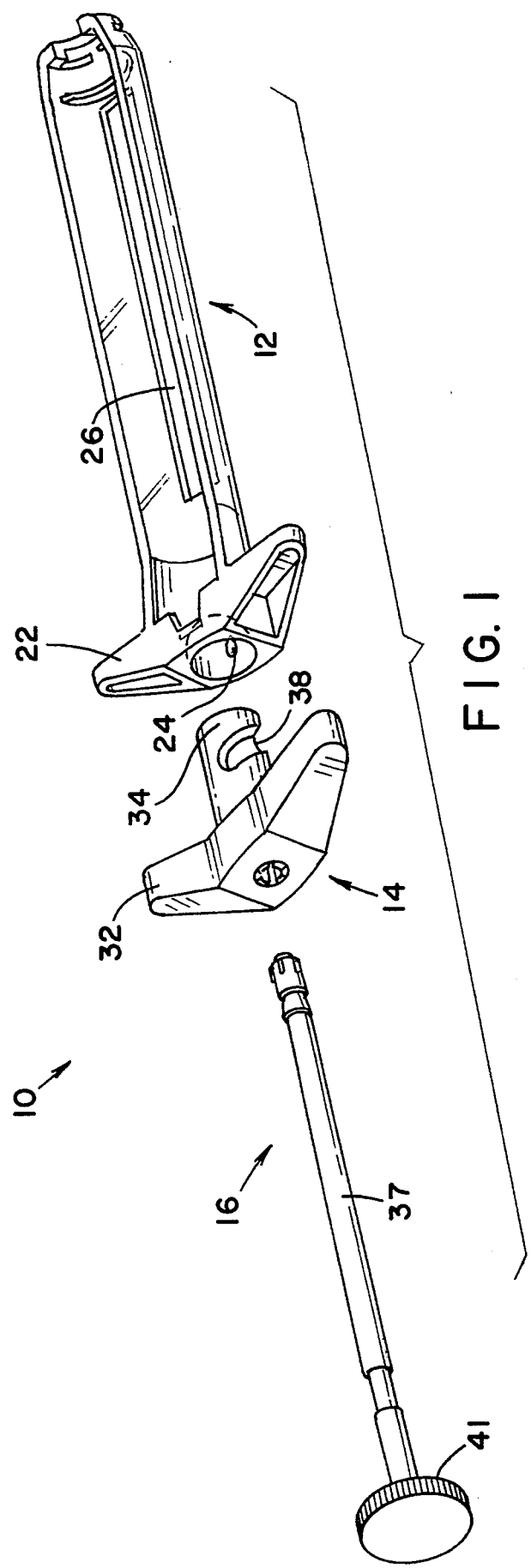
FIG. 1 is an exploded perspective view of a preferred syringe holder of the invention.

Referring to FIG. 1, the syringe holder of the invention, represented by 10, is intended for use in combination with conventional medicament-containing ampoules, not illustrate herein, which are closed at the upper end with a flexible piston slidable within the bore of the ampoule and closed at the lower necked-down end by a rubber diaphragm secured to the ampoule by a crimped-on metal collar. The necked-down end is conventionally fitted with a needle/needle hub unit and a needle sheath. A typical such ampoule/needle assembly is sold commercially as CARPUJECT ®.

In preferred embodiments, the syringe holder comprises a total of three elements, namely, a generally semi-cylindrical body or hollow frame portion 12, a clamping element 14, and a plunger element 16.

Figure 2A:
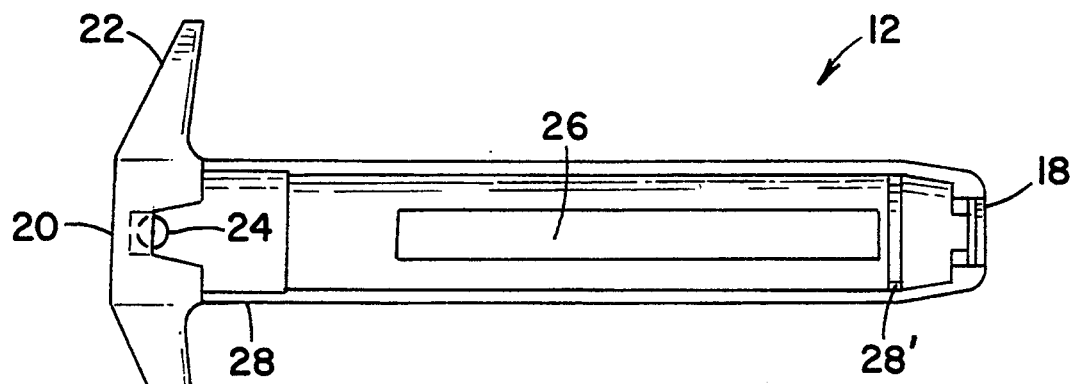
FIGS. 2A and 2B are a plan view and a side elevational view partially in section, respectively, of the frame portion of a syringe holder of the invention.
Figure 2B:
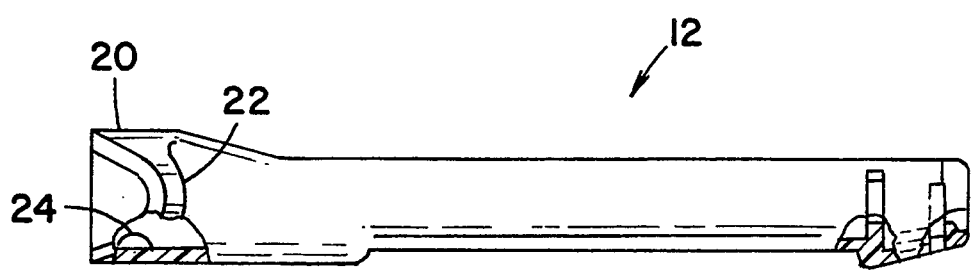

With reference to FIGS. 2A and 2B, the body portion comprises a generally semi-cylindrical unit which is adapted for side-loading of an ampoule through the open side wall. For this purpose, the lower end has a side opening slot 18, sized to fit around the needle hub of an ampoule/needle/needle hub/needle sheath unit used in combination with the holder. The upper end of the body portion has a short cylindrical section having a bore 20 therethrough for receiving clamping element 14. Finger gripping means 22 are provided for ease of manipulation.

An important feature of this invention is that the head portion of the body is provided on its inside surface with a lug 24 the purpose of which is described in further detail herein below. The lug is preferably hemispherical and can conveniently be molded integrally with the body, thus eliminating the need for additional molding and sealing of the lug or a boss element to the body.

The holder may also have a viewing window 6, which is particularly desirable when the syringe holder is used as an aspirating syringe and the body is fabricated of a material which does not exhibit good transparency. The body portion optionally can be equipped with raised ribs 28 or 28' located near the upper or lower end, respectively, of the body portion, which serve to align an ampoule within the body of the syringe holder with the tip of the piston engaging means 40.

Figure 3A:
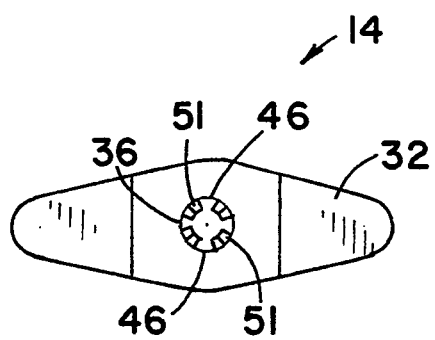
FIGS. 3A, 3B and 3C are an end view, a plan view and a cross-sectional view, respectively, of the clamping element of a syringe holder of the invention.
Figure 3B:
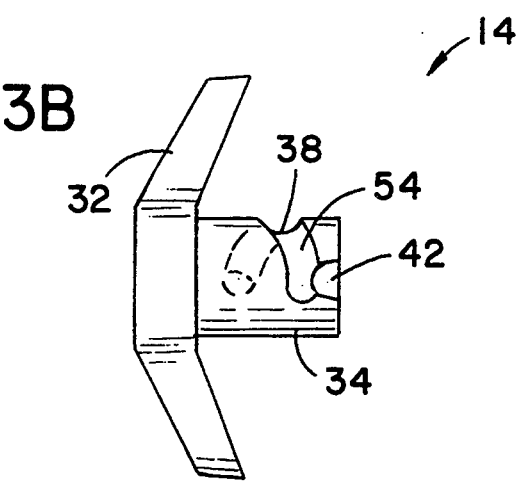
Figure 3C:
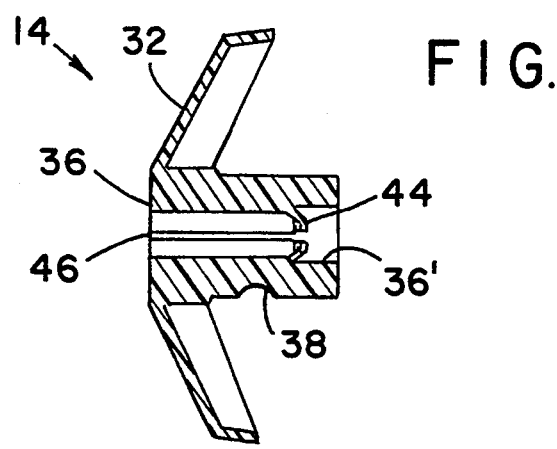
Figure 4A:
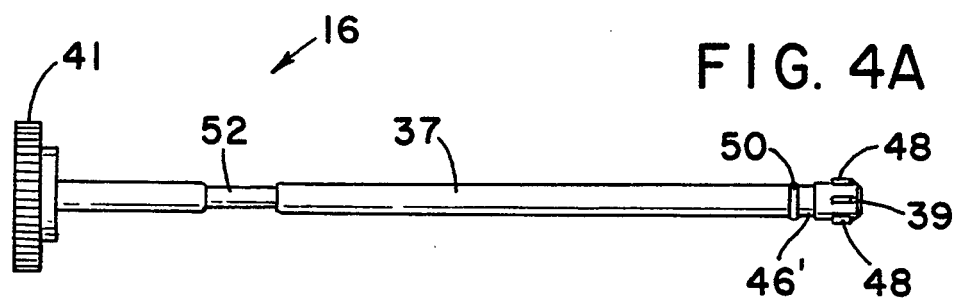
FIGS. 4A and 4B are plan and end views, respectively, of the plunger element of a syringe holder of the invention.
Figure 4B:
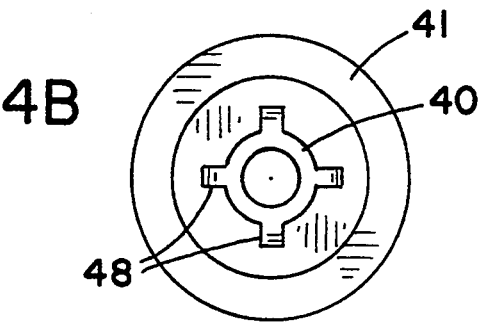

The ampoule clamping element shown in FIGS. 3A, 3B and 3C consists of a pair of handles 32 and a barrel 34 having a relatively small diameter bore 36 sized to slidably receive at least the shaft 37, and preferably both the shaft and head portions 39 of plunger element 16 shown in FIGS. 4A and 4B. The barrel of clamping element 14 has a slightly expanded bore section 36' which is sized to accept piston engaging means 40 and which has a slightly larger diameter than the shaft portion of the plunger. Extending partially around the outer surface of clamping element 14 is a helical groove 38. Helical groove 38 is semi-circular in cross section and is of such width and depth that it will slidably receive hemispherical lug 24 on the inside surface of the head portion of body 12 when the clamping element is appropriately, i.e. slidably inserted into the body.

The plunger element preferably consists of a unitary injection moldable structure. However, the piston engaging means 40 and/or the actuation button 41 may be affixed to the rod after the rod has been inserted through the bore of the clamping element.

An essential feature of this invention is that the barrel portion of the clamping element is provided with ramp means 42 connecting the lower part of helical groove 38 with the lower surface of the clamping element. Helical groove 38 is slidably accessible to hemispherical lug through ramp means 42 and engageable with the lug in such a manner so as to secure the clamping element to the body portion such that all the elements of the syringe holder are in cooperative engagement with one another.

In particularly preferred embodiments of the invention, clamping element 14 is provided with fingers 44 and grooves 46 on the inside diameter of bore 36, the distal portion of rod 37 is provided with fins 48, and the distal portion of rod 37 is provided with undercut means 46'. When inserted through the bore, the fins travel through the grooves and the head of the rod is capable of flexing the fingers. The fingers are engageable with the undercut means to capture the plunger element in the clamping element. The fins simulate a larger head diameter engageable with the ampoule, which is desirable, while the smaller rod diameter reduces drag for aspiration and minimizes undesirable relaxation of the fingers, for example, that which can result during high temperature sterilization. Keying means 51 can be provided so that the fins align themselves with the grooves upon insertion of the distal portion of the plunger element into the bore. The rod can be provided with radial ribs 50 which retain the plunger rod in the rear position and aid in cartridge ejection, and detent means 52 which functions to minimize undesirable relaxation of the fingers.

As noted above, the various parts of the syringe holder can be readily assembled. For example, plunger element 16 can be inserted through the bore of clamping element 14 in a "one way" or "insert only" manner. The resulting clamping element/plunger element subassembly can then be inserted into the bore of body portion 12. The clamping element is rotated so that the ramp means engages the hemispherical lug on the inside surface of the body portion. The clamping element is then pressed into the body such that the hemispherical lug slides through the ramp means and acquires access to the helical groove. All the elements of the syringe holder are thereby joined together in cooperative relationship with one another. It is a particularly advantageous feature of this invention that a syringe holder is provided containing just three working parts which can be easily assembled merely by snapping together the various pieces. This avoids the costly and undesirable step of gluing, mechanically attaching, and/or thermal, sonic or solvent welding the pieces together.

By rotating the clamping element approximately one half revolution in one direction or the other, the clamping element can move either forward to a fully engaged position or backward to a fully retracted position. In use, the clamping element is first fully retracted by one half turn in one direction, an ampoule/needle/needle hub/needle sheath unit is inserted through the side opening of the syringe holder, and the clamping element is given one half turn in the opposite direction to cause the shoulder of the clamping element to bear against the rim of the ampoule, thus securing it firmly in place within the holder. The plunger is then engaged with the piston of the ampoule. One means of achieving such engagement is to turn the plunger rod so as to engage a screw threaded hole in the end of the piston engaging means 40 with a screw-threaded post on the piston. The clamping element may optionally be equipped with a pair of raised ribs 54 located near both ends of helical groove 38 which serve to lock the clamping element in the fully engaged or fully retracted positions.

Although the various elements of the syringe holders described herein may be made of any suitable material including metals or plastics, they are well adapted to fabrication of plastic. In particular, body portion 12, clamping element 14 and plunger element 16 can be fabricated by known precision injection molding techniques. When the various elements are constructed of plastic, suitable plastics include high density polypropylene, polycarbonate, polystyrene, ABS (clear or opaque), nylon, acetals such as DELRIN ® or polyethylene. It is particularly advantageous that the body portion be fabricated of a transparent material so that the ampoule is visible during operation. The plastic preferably is injection moldable. As noted, a particularly advantageous feature of this invention is that the various pieces of the syringe holder, i.e., the body, clamping element and plunger element can be easily and economically manufactured in large quantities by known precision injection molding techniques. When the holder is intended for use in a high temperature sterilization process, the plastic preferably is substantially resistant to deformation at sterilization temperatures.

It will be appreciated that minor modifications in the various elements of the invention may be made without departing from the spirit of the invention. For example, the piston engaging means is described herein as being a screw-threaded element which mates with a screw-threaded post on the ampoule piston. Such means of engaging the plunger with the piston is a preferred means, however, other piston engaging means well known in the art, such as, for example, multiple retractable claws or hooks, fixed claws, an expandable chuck, resilient gripping fingers, a harpoon, or a bayonet connection will serve the purpose as well.

The invention has been described in detail with particular reference to certain preferred embodiments thereof, but it will be understood that variations and modifications can be effected within the spirit and scope of the invention.

What is claimed is:

1. An injection molded hypodermic syringe holder adapted to receive a disposable medicament-containing ampoule including a bore and a piston within said bore, said syringe holder comprising
   a semi-cylindrical hollow frame portion shaped to receive an ampoule and having a generally cylindrical portion having on the frame side of its inside surface a projecting lug and a cut-away portion opposite said lug;
   an axially movable clamping element rotatable about its longitudinal axis within the cylindrical portion of said frame portion and engageable with an associated ampoule to securely immobilize the ampoule within the frame portion of the syringe holder, said clamping element comprising a barrel portion at the distal end and thereof, a handle portion at the proximal end thereof, a helical groove on the outer surface of said barrel portion, a bore therethrough, and ramp means for permitting said lug to access said helical groove connecting said helical groove with the distal end surface of said clamping element; said barrel portion being sized to rotate and translate within said cylindrical head;
   a plunger element having a rod portion having on its distal end a piston engaging means for engaging the piston of said ampoule, said rod portion and piston engaging means being axially slidable and receivable within said bore of said clamping element;
   wherein said lug can be slided through said ramp means to access and engage said helical groove, whereby said lug secures the clamping element to said frame portion such that all of the elements of the syringe holder are in cooperative engagement with one another.

2. The syringe holder of claim 1 wherein said clamping element is provided with flexible fingers on the inside diameter of said bore and the distal portion of the rod is provided with undercut means for capturing said plunger element in said clamping element, said rod being inserted through said bore and capable of flexing said fingers, said fingers being engaged with said undercut means to capture said plunger element in said clamping element.

3. The syringe holder of claim 1 wherein said clamping element further comprises fingers and grooves on the inside diameter of said bore and the distal end of said rod is provided with fins and undercut means for capturing said plunger element in said clamping element.

4. The syringe holder of claim 2 wherein said rod portion is provided with radial ribs and detent means for minimizing relaxation of said fingers.

5. The syringe holder of claim 1 wherein said piston comprises a screw threaded post and said piston engaging means comprises a screw-threaded hole in the end thereof for screw-threaded engagement with said screw threaded post.

6. The syringe holder of claim 1 having raised ribs within said helical groove near both ends thereof for locking said clamping element in either a fully engaged or fully retracted position.

7. The syringe holder of claim 1 wherein said body portions, said clamping element and said plunger element are fabricated of plastic.

* * * * *